Figure 1:
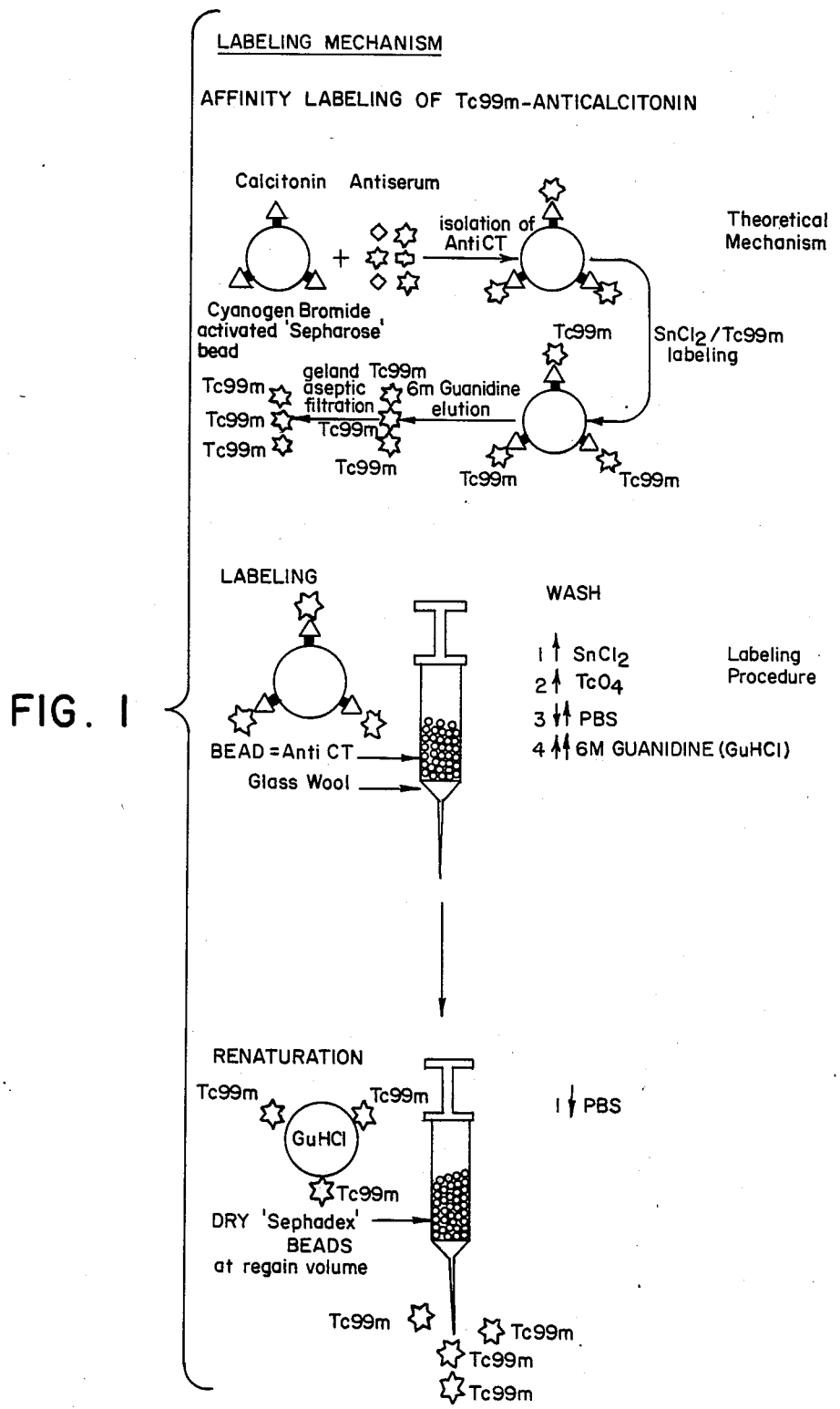

United States Patent [19]

Best

[11] Patent Number: 4,676,973
[45] Date of Patent: Jun. 30, 1987

[54] METHOD FOR DIAGNOSING LUNG ABNORMALITIES USING RADIOLABELLED AGENTS

[76] Inventor: Mark P. Best, 146 Caversham Valley Road, Dunedin, New Zealand

[21] Appl. No.: 602,332

[22] Filed: Apr. 20, 1984

[30] Foreign Application Priority Data

Apr. 20, 1983 [NZ] New Zealand .................. 203949

[51] Int. Cl.⁴ .................. A61K 43/00; A61K 49/00
[52] U.S. Cl. .................. 424/1.1; 424/9; 935/107
[58] Field of Search .................. 424/1.1, 9; 935/107

[56] References Cited

U.S. PATENT DOCUMENTS

| | | | |
|---|---|---|---|
| 4,280,991 | 7/1981 | Burch | 424/1.1 |
| 4,444,744 | 4/1984 | Goldenberg | 424/1.1 |
| 4,514,506 | 4/1985 | Braatz et al. | 424/88 |

OTHER PUBLICATIONS

Best et al., "Clinical Nuclear Medicine", vol. 10, No. 4, Apr. 1985, p. 297.
Best et al., "Journal of Nuclear Medicine", 25, p. 18 (1984).
Scott, Diss. Abst. Int. B, 44(4) 1983, p. 1054.
Tzeng, Diss. Abst. Int. B, 44(4) 1983, p. 1068.
Radcliffe, from *Markers for Diagnosis and Monitoring of Human Cancer*, Serono Symposia, vol. 46, Colnaghi et al., Eds., Academic Press, Ing, London, 1982, pp. 85–94.

*Primary Examiner*—Christine M. Nucker
*Attorney, Agent, or Firm*—Birch, Stewart, Kolasch and Birch

[57] ABSTRACT

Epithelial lung tumors are known to produce specific biological substances such as hormones. Radiolabelled antibodies to such substances are prepared and ventilated by a subject. Deposition of the radiolabelled antibodies occurs in the respiratory air passages and with controlled particle size and inhalation particularly in the tracheo-bronchial tree.

The antibodies react antigenically with the biological substances, becoming localized at the tumor sites. Concentrations of radiolabelled antibodies may be detected using ratio detection means such as a gamma camera.

7 Claims, 1 Drawing Figure

METHOD FOR DIAGNOSING LUNG ABNORMALITIES USING RADIOLABELLED AGENTS

BACKGROUND OF INVENTION

This invention relates to a method of diagnosing lung disorders, particularly epithelial lung tumors. It is known that these tumors produce bioactive substances particularly hormones. It has been the goal of workers to use radiolabelled antibodies to such substances to permit detection of tumors.

One such substance is the hormone calcitonin. According to this invention, antibodies to calcitonin are prepared and labelled with technetium 99 m. These radiolabelled antibodies are prepared as an aerosol which is ventilated by a subject. The particle size is controlled to permit maximum deposition by sedimentation, rather than impaction. The antibodies are localised by immunoreactivity in proximity to the tumor site. Mucociliary clearance removes unbound radiolabelled antibodies. The subject is then subjected to a radio detection means which locates concentration of labelled antibody indicating areas of abnormal hormone production, or tumor sites.

SUMMARY OF THE INVENTION

According to one embodiment of the present invention there is provided a method of diagnosing an abnormality in a patient's lung comprising subjecting a patient to radiolabelled agent by ventilation, the radiolabelled agent being retained at the locality of the abnormality but being otherwise removed from the lung by a body function, the patient then being subjected to a radio detection means adapted to record the presence of the retained agent and thereby provide diagnostic information.

BRIEF DESCRIPTION OF THE DRAWING

The present invention will now be described by way of example and with reference to the accompanying drawings wherein FIG. 1: shows diagrammatically the preparation of affinity purified antisera against calcitonin, linked to cyanogen bromide activated sepharose. Labelled antibodies were recovered using 6M Guanidine in phosphate buffered saline and dialysed. Labelling with technetium 99 m was by stannous reduction and immunoreactivity confirmed by radioimmunioassay and immunodiffusion.

BRIEF DESCRIPTION OF THE PREFERRED EMBODIMENT

Antibodies prepared according to the method shown in FIG. 1. 150 milligrams of labelled antibody is delivered to the lungs in an aerosol generated by a compressed air nebuliser and passed through drying and sedimentation chambers. The particle size is controlled such that approximately 60% of the particles have a diameter within the range 0.2 to 1.4 microns. The patient is caused to inhale this aerosol, which is delivered at low velocity by shallow breathing. Deposition of the aerosol on the lung surfaces occurs, with normal mucociliary clearance acting to remove the aerosol. Concentrations of calcitonin occur around the tumor sites. Twenty four hours is allowed to elapse to permit mucociliary clearance to remove extraneous unreacted antibody, which time has found to provide maximum contrast between localised antibody and background.

The subject is then photographed using a gamma camera which shows up concentrations of radiolabelled antibody, concentrated around tumor sites.

The resulting diagnosis is believed to be more accurate than of the two available techniques, providing higher resolution data, and with minimal discomfort to the patient.

Where in the aforegoing description reference has been made to specific components or integers of the invention having known equivalents then equivalents are herein incorporated as if individually set forth.

Although this invention has been described by way of example and with reference to possible embodiments thereof it is to be understood that modifications or improvements made be made thereto without departing from the scope of the invention as defined in the appended claims.

I claim:

1. A method of diagnosing abnormalities in a patient's lung, comprising:

administering to a patient as an aerosol a radiolabelled agent by ventilation, said radiolabelled agent being an antibody specific to an antigen produced by a tumor and labelled with a radioactive isotope;

waiting a sufficient amount of time to allow mucociliary clearance of unreacted radiolabelled antibody; and detecting by detection means the presence of the radiolabelled agent.

2. The diagnostic method as in claim 1, wherein said antigen is calcitonin.

3. The diagnostic method as in claim 1, wherein said radioactive isotope is technetium 99 m.

4. The diagnostic method as in claim 1, wherein said antigen is calcitonin and said radioactive isotope is technetium 99 m.

5. The diagnostic method as in claim 1, wherein the particles in said aerosol have a particle size of from 0.2 to 1.4 microns.

6. The diagnostic method as in claim 1, wherein the detection means comprises a gamma camera.

7. The diagnostic method as in claim 1, wherein twenty-four hours is allowed to elapse to permit mucociliary clearance to remove unreacted antibody.

* * * * *